(12) United States Patent
Abels et al.

(10) Patent No.: US 7,857,618 B2
(45) Date of Patent: Dec. 28, 2010

(54) ORTHODONTIC BRACKET INCLUDING MECHANISM FOR REDUCING SLOT WIDTH FOR EARLY TORQUE CONTROL

(75) Inventors: Norbert Abels, Homburg (DE); Claus H. Backes, Saarbrücken (DE)

(73) Assignee: Ultradent Products, Inc., South Jordan, UT (US)

( * ) Notice: Subject to any disclaimer, the term of this patent is extended or adjusted under 35 U.S.C. 154(b) by 182 days.

(21) Appl. No.: 11/945,801

(22) Filed: Nov. 27, 2007

(65) Prior Publication Data

US 2009/0136889 A1  May 28, 2009

(51) Int. Cl.
*A61C 7/30* (2006.01)
(52) U.S. Cl. ....................................................... 433/11
(58) Field of Classification Search ................ 433/8–11, 433/13, 15–16, 18
See application file for complete search history.

(56) References Cited

U.S. PATENT DOCUMENTS

| | | |
|---|---|---|
| 2,265,420 A | 12/1941 | Brusse et al. |
| 3,327,393 A | 6/1967 | Brader |
| 4,531,911 A | 7/1985 | Creekmore |
| 4,551,094 A | 11/1985 | Kesling |
| 4,784,606 A | 11/1988 | Jones et al. |
| 4,799,883 A * | 1/1989 | Stoller et al. .................. 433/17 |
| 5,062,794 A | 11/1991 | Miura |
| 5,078,596 A | 1/1992 | Carberry et al. |
| 5,127,828 A | 7/1992 | Suyama |
| 5,145,365 A | 9/1992 | Farzin-Nia et al. |
| 5,154,607 A | 10/1992 | Hanson |
| 5,160,261 A | 11/1992 | Peterson |
| 5,232,361 A | 8/1993 | Sachdeva et al. |
| 5,238,403 A | 8/1993 | Schudy |
| 5,242,299 A | 9/1993 | Yoshida |
| 5,261,814 A | 11/1993 | Farzin-Nia et al. |
| 5,263,858 A | 11/1993 | Yoshida et al. |
| 5,282,743 A | 2/1994 | Miura |
| 5,299,934 A | 4/1994 | Suyama |
| 5,302,116 A | 4/1994 | Viazis |
| 5,318,440 A | 6/1994 | Adam et al. |

(Continued)

FOREIGN PATENT DOCUMENTS

CN  2557100  6/2003

(Continued)

OTHER PUBLICATIONS

Redlich, M. et al., In vitro study of frictional forces during sliding mechanics of "reduced-friction" brackets, http://cat.inist.fr/?aModele=afficheN&cpsidt=14982715, 2006 INIST-CNRS.

*Primary Examiner*—Chris L Rodriguez
*Assistant Examiner*—Michael R Ballinger
(74) *Attorney, Agent, or Firm*—Workman Nydegger

(57) ABSTRACT

Orthodontic brackets include a bracket base, at least one arch wire slot formed in the base adapted to receive an arch wire therein, and a moveable structure for selectively narrowing the width of at least a portion of the arch wire slot so as to allow for engagement of an undersized arch wire having a width less than the slot width. The moveable structure for selectively narrowing the width of the arch wire slot may be defined by one or more spaced apart cuts disposed in at least one side wall defining the arch wire slot so as to define a bendable portion of the sidewall.

20 Claims, 15 Drawing Sheets

U.S. PATENT DOCUMENTS

| | | |
|---|---|---|
| 5,470,228 A | 11/1995 | Franseen et al. |
| D367,116 S * | 2/1996 | Viazis ................... D24/180 |
| 5,613,849 A | 3/1997 | Tanaka et al. |
| 5,707,231 A | 1/1998 | Watt et al. |
| 5,711,666 A | 1/1998 | Hanson |
| 5,727,941 A | 3/1998 | Kesling |
| 5,738,513 A | 4/1998 | Hermann |
| 5,813,852 A | 9/1998 | Kawaguchi |
| 5,906,486 A | 5/1999 | Hanson |
| 5,971,753 A * | 10/1999 | Heiser ..................... 433/11 |
| 6,042,373 A * | 3/2000 | Hermann .................. 433/13 |
| 6,164,964 A | 12/2000 | Nakagawa |
| 6,168,429 B1 | 1/2001 | Brown |
| 6,257,882 B1 | 7/2001 | Wyllie, II |
| 6,302,688 B1 | 10/2001 | Jordan et al. |
| 6,358,043 B1 | 3/2002 | Mottate et al. |
| 6,582,226 B2 | 6/2003 | Jordan et al. |
| 6,644,968 B2 | 11/2003 | Orikasa et al. |
| 6,648,638 B2 | 11/2003 | Castro et al. |
| 7,014,460 B2 | 3/2006 | Lai et al. |
| 7,063,531 B2 | 6/2006 | Maijer et al. |
| 7,131,836 B1 | 11/2006 | Kesling |
| 7,134,873 B2 | 11/2006 | Miyaji et al. |
| 7,140,875 B2 | 11/2006 | Lai et al. |
| 7,140,876 B2 | 11/2006 | Cinader et al. |
| 7,192,274 B2 | 3/2007 | Stadtmiller et al. |
| 2002/0197581 A1 | 12/2002 | Georgakis et al. |
| 2005/0255422 A1 | 11/2005 | Cordato |
| 2005/0277083 A1 | 12/2005 | Lai |
| 2006/0014116 A1 | 1/2006 | Maijer et al. |
| 2006/0172248 A1 | 8/2006 | Sernetz et al. |
| 2006/0172249 A1 | 8/2006 | Lai et al. |
| 2006/0228662 A1 | 10/2006 | Lokar et al. |
| 2006/0228664 A1 | 10/2006 | Castner et al. |
| 2006/0257809 A1 | 11/2006 | Tsunori |
| 2006/0257810 A1 | 11/2006 | Maijer et al. |
| 2006/0263737 A1 | 11/2006 | Oda |
| 2006/0269895 A1 | 11/2006 | Voudouris |
| 2007/0015104 A1 | 1/2007 | Wiechmann et al. |
| 2007/0184399 A1 | 8/2007 | Salich |
| 2007/0224568 A1 | 9/2007 | Lin |

FOREIGN PATENT DOCUMENTS

| | | |
|---|---|---|
| EP | 1184005 | 3/2002 |
| WO | WO 2006/073699 | 7/2006 |
| WO | 2008003212 | 1/2008 |

* cited by examiner

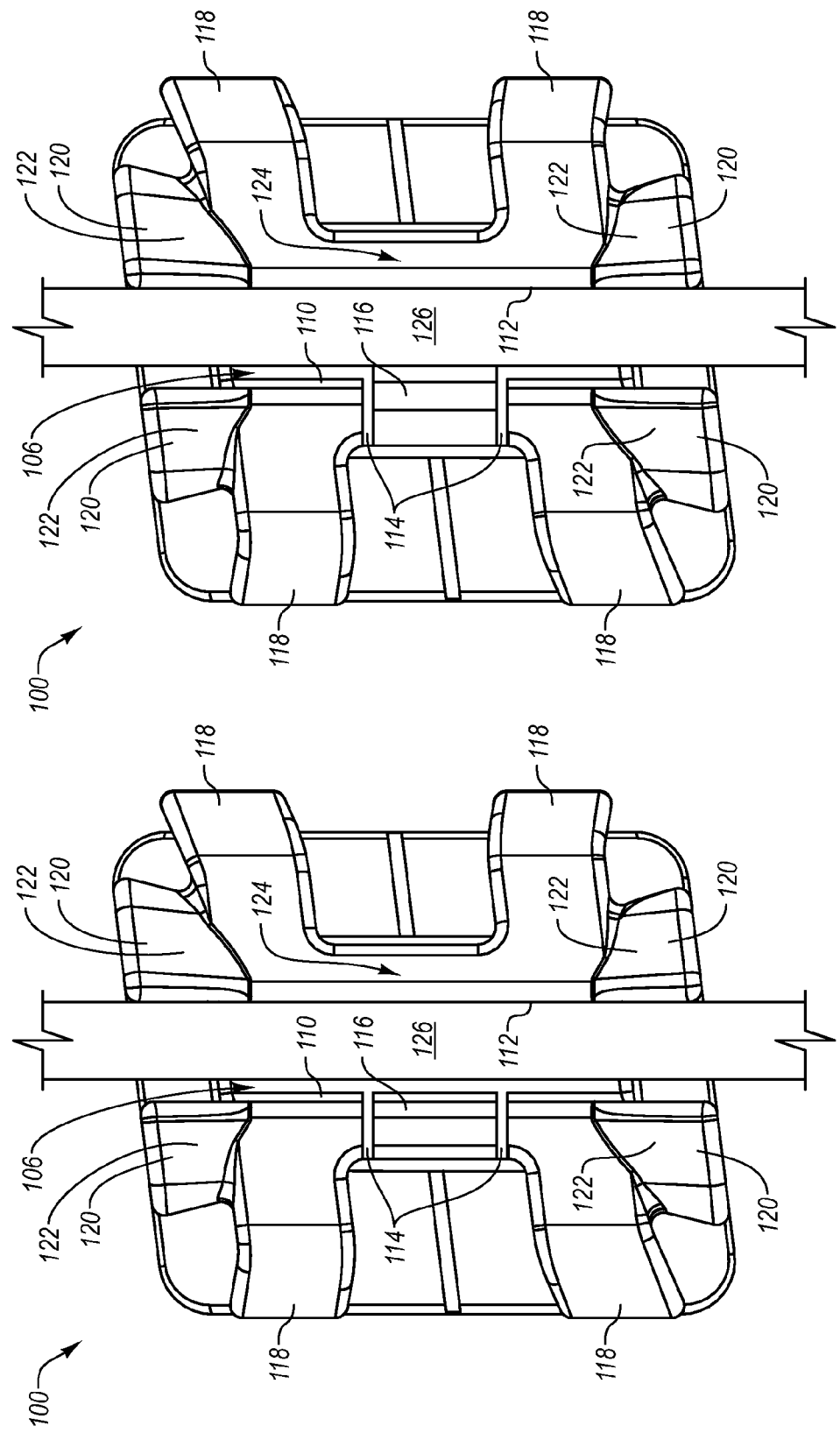

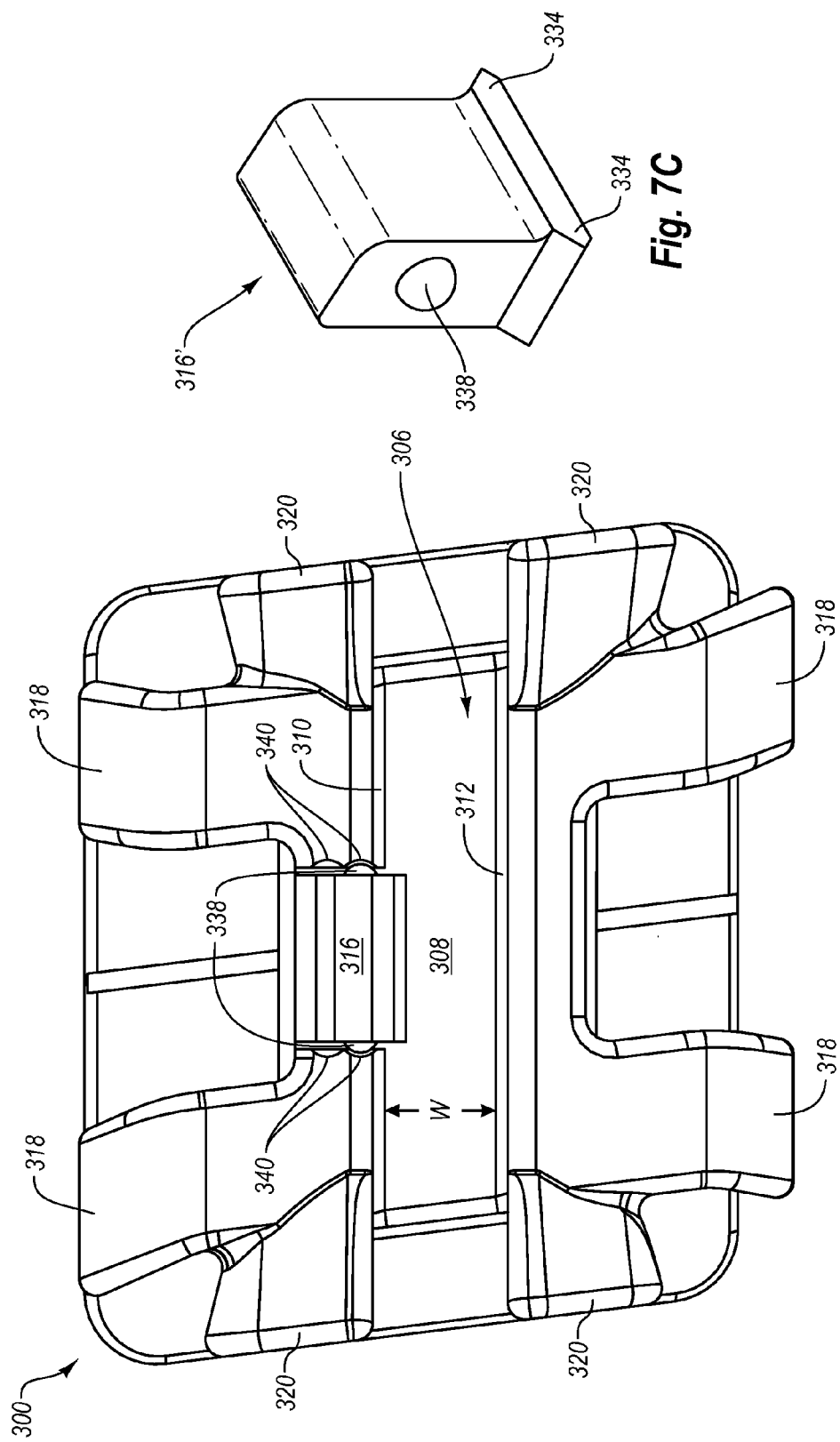

ORTHODONTIC BRACKET INCLUDING MECHANISM FOR REDUCING SLOT WIDTH FOR EARLY TORQUE CONTROL

BACKGROUND OF THE INVENTION

1. The Field of the Invention

The present invention relates to orthodontic brackets that include a bracket base and at least one slot for receiving an arch wire as well as a feature for early torque control.

2. The Relevant Technology

Orthodontics is a specialized field of dentistry that involves the application of mechanical forces to urge poorly positioned, or crooked, teeth into correct alignment and orientation. Orthodontic procedures can be used for cosmetic enhancement of teeth, as well as medically necessary movement of teeth to correct overjets or overbites. For example, orthodontic treatment can improve the patient's occlusion, or enhanced spatial matching of corresponding teeth.

The most common form of orthodontic treatment involves the use of orthodontic brackets and wires, which together are commonly referred to as "braces." Orthodontic brackets, more particularly the orthodontic bases, are small slotted bodies configured for direct attachment to the patient's teeth or, alternatively, for attachment to bands which are, in turn, cemented or otherwise secured around the teeth. Once the brackets are affixed to the patient's teeth, such as by means of glue or cement, a curved arch wire is inserted into the slot of each bracket. The arch wire acts as a template or track to guide movement of the teeth into proper alignment.

There are two distinct classes of orthodontic brackets: those that require the use of ligatures to fasten the arch wire to the bracket, and those that are self-ligating. In brackets of the first class, small ligature wires or elastics are typically used to hold the arch wire in a securely seated position in the brackets. Ligatures or some other form of fastening means are essential to ensure that the tensioned arch wire is properly positioned around the dental arch, and to prevent the wire from being dislodged from the bracket slots during chewing of food, brushing of teeth, or application of other forces. One type of commercially available ligature is a small, elastomeric O-ring, which is installed by stretching the O-ring around small wings known as "tie wings" that are connected to the bracket body. Metal ligatures are also used to retain arch wires within the bracket slots.

In an effort to simplify the process of installing braces, a variety of self-ligating brackets have been developed. The term "self-ligating bracket" refers to a class of orthodontic brackets that include some sort of cover, whether separate from, hingedly or otherwise attached to the base, which encloses or otherwise retains the arch wire within the slot of the base.

In either case, there is a need during treatment to apply various corrective forces to the teeth during treatment. Arch wires having different cross-sectional configurations are typically used to apply different forces, depending on the corrective movement to be achieved. Arch wires typically have either a square, rectangular, or round cross-section. Square and rectangular cross-sections allow the arch wire to be used to apply a torquing force when engaged in an arch wire slot of an orthodontic bracket. Torquing forces provide for tooth movement in the labial and/or lingual directions. Although a wire having a round cross-section does not allow application of torquing forces when engaged within an arch wire slot, it does provide a greater degree of flexibility and generally requires less force to effect movement, which is more comfortable for the patient. As such, round wires are often useful during the beginning stages of orthodontic treatment when the teeth are most malaligned. Use of such a round arch wire allows for movement of teeth to correct spacing and alignment issues with relatively light (and more comfortable) forces. Once these corrections have been achieved, a square or rectangular wire typically replaces the round arch wire, so as to allow torquing of selected teeth to complete the treatment.

As such, treatment often progresses in a series fashion, in which spacing and alignment issues are first addressed, and tooth movement in the labial and/or lingual directions is addressed afterwards. Although such treatment regimes work, they can take several months to complete. As such, it would be an improvement in the art to provide an orthodontic bracket which could be easily manufactured, and which would include a mechanism for allowing application of relatively light forces (i.e., similar to those applied by a round arch wire), but which forces are also capable of applying a corrective torquing force. Such a bracket would be expected to provide movement of teeth to correct spacing and alignment with light forces, while simultaneously providing torquing movements, which would provide for faster overall treatment times, while also providing increased comfort for the patient during torquing correction.

BRIEF SUMMARY OF THE PREFFERED EMBODIMENTS

The present invention is directed to an orthodontic bracket including a bracket base, and at least one arch wire slot formed in the base adapted to receive an arch wire therein. The arch wire slot is defined by sidewalls disposed on the occlusal and gingival sides of the slot, as well as a bottom surface so that the slot is open towards the labial side. The bracket further includes means for selectively narrowing the width of at least a portion of the arch wire slot so as to allow for engagement of an undersized arch wire having a width less than the slot width.

In one embodiment, the means for selectively narrowing the width of the arch wire slot comprises one or more spaced apart cuts disposed in one sidewall along one side of the arch wire slot so as to define a bendable portion of the sidewall between the spaced apart cuts. The bendable portion is selectively inwardly bendable so as to narrow the occlusal-gingival width of at least a portion of the slot width. Such a configuration advantageously allows a practitioner to insert an undersized light force wire (i.e., a wire having a width that is less than the occlusal-gingival width of the arch wire slot), and then bending the bendable portion of the bracket so as to engage the arch wire against the bendable portion on one side, the bottom surface of the arch wire slot, and the opposite side wall of the arch wire slot. In an alternative embodiment, the means for selectively narrowing the width of the arch wire slot may comprise a movable portion of at least one sidewall defining the arch wire slot which is configured to be selectively moved by the practitioner (e.g., slide inwardly) so as to narrow at least a portion of the slot.

In another embodiment, the bracket includes an arch wire slot defined by oppositely disposed sidewalls on either side of the arch wire slot in which the side walls are substantially continuous such that the slot width is substantially constant along its entire mesial-distal length. In such an embodiment, the side walls are substantially continuous except from at least one sidewall including one or more spaced apart cuts disposed in one or both sidewalls so as to define at least one bendable portion of the sidewall (e.g. between two spaced apart cuts). In such an embodiment, the bendable portion(s)

are selectively bendable inwardly so as to narrow the width of at least a portion of the arch wire slot. In other words, such an embodiment may include bendable portions formed in both the occlusal side wall and in the gingival side wall, providing greater flexibility to the practitioner so as to allow for bending of either (or both) bendable portions.

In each of the described embodiments, the bracket includes means for selectively narrowing the width of the arch wire slot so as to engage an undersized arch wire. Such embodiments advantageously allow for use of a rectangular arch wire having a width that is less than those conventionally used (e.g. 0.018 or 0.022 inch), but which can still be sufficiently engaged by the arch wire slot so as to provide for corrective movement of the teeth, including torquing corrective movements. Use of such a smaller wire allows for the same corrective movements of a larger wire, but with less force and better comfort to the patient.

Advantageously, larger, conventional width wires may also be used with the same bracket, for example, after use of the smaller width lighter force wire by simply repositioning the bendable portion(s) of the sidewall(s) to their original configurations and inserting the larger arch wire. Such would not be the case with a custom bracket configured with an arch wire slot having a width smaller than the conventional 0.018 or 0.022 inch widths. In addition, the engagement of the bendable portion of the sidewall with the arch wire typically represents only a fraction of the full mesial-distal length of the arch wire slot, so that even less sliding friction force is present than would exist if the full length of the arch wire slot were simply formed so as to have a width smaller than the conventional 0.018 or 0.022 inch width. Preferably, the one or more bendable portions are located at or near the center of the occlusal and/or gingival side walls.

In addition, the bracket may be configured so as to provide for variable active-passive ligation such that the practitioner may choose to apply active or passive ligation between a ligature engaged with the bracket and the arch wire engaged within the arch wire slot. Active ligation is defined as a configuration in which the ligature engages the arch wire, pressing it downward towards the lingual bottom surface of the bracket. Passive ligation is defined as a configuration in which the ligature is held so as to be spaced apart from the arch wire so that the arch wire may slide more freely within the slot (i.e., sliding friction is reduced). The bracket is configured so that the practitioner may easily switch from active to passive ligation and vice-versa.

In order to provide such functionality, according to one embodiment, a non self-ligating bracket according to the invention may include a plurality of end wing extensions disposed on the bracket base and that extend outwardly from the bracket base in a mesial-distal direction substantially parallel to the arch wire slot. The end wing extensions may extend substantially perpendicular relative to corresponding tie wings which extend substantially in a gingival-occlusal direction. In order to achieve passive ligation, the ligature is positioned by the practitioner so as to be supported on a labial top surface of the end wing extensions, holding the ligature so as to be spaced apart from the arch wire engaged within the arch wire slot. For active ligation, the ligature is simply pushed off the mesial and distal ends of the end wing extensions so as to no longer be supported by the end wing extensions, in which position the ligature engages the arch wire, pressing it down (i.e., lingually) within the arch wire slot.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 3A is a top view similar to FIG. 2B, but with an undersized rectangular arch wire received within the slot of the bracket;

FIG. 3B is a top view of the bracket and arch wire of FIG. 3A in which the bendable portion within one sidewall has been bent inwardly so as to engage a portion of the undersized rectangular arch wire;

FIG. 7B is a labial top view of the bracket of FIG. 7A in which a portion within one sidewall has been moved inwardly;

FIG. 7C is a perspective view of an the movable portion of the bracket of FIGS. 7A and 7B;

DETAILED DESCRIPTION OF THE PREFERRED EMBODIMENTS

I. Introduction

The present invention is directed to an orthodontic bracket including a bracket base, at least one arch wire slot formed in the base adapted to receive and arch wire therein, and means for selectively narrowing the width of at least a portion of the arch wire slot so as to allow for engagement of an undersized arch wire having a width less than the slot width. The arch wire slot is defined by sidewalls disposed on either side of the slot.

II. Exemplary Orthodontic Brackets

Figure 1:
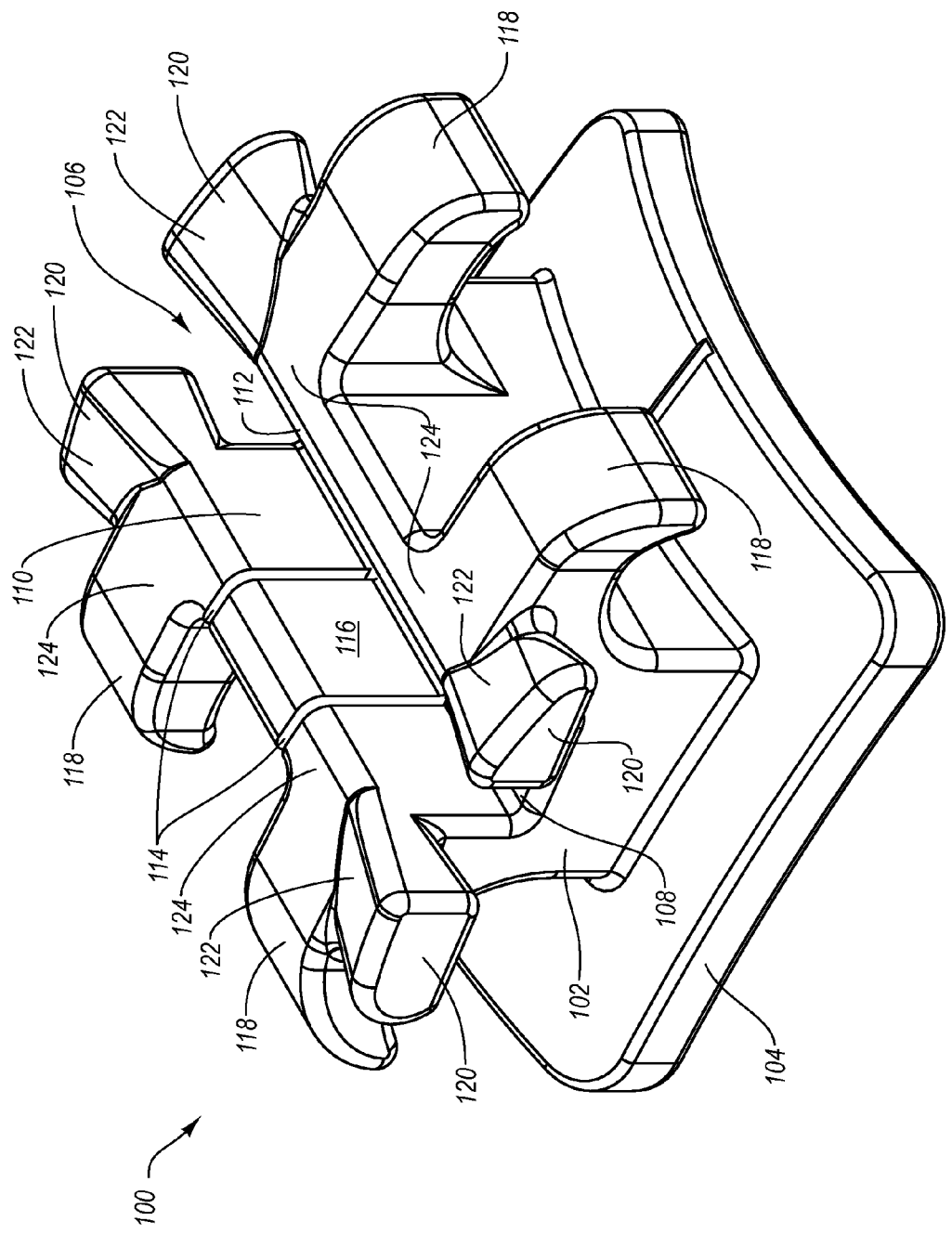
FIG. 1 is an isometric view of an exemplary bracket according to the present invention including a mechanism for selectively reducing arch wire slot width.
Figure 2A:
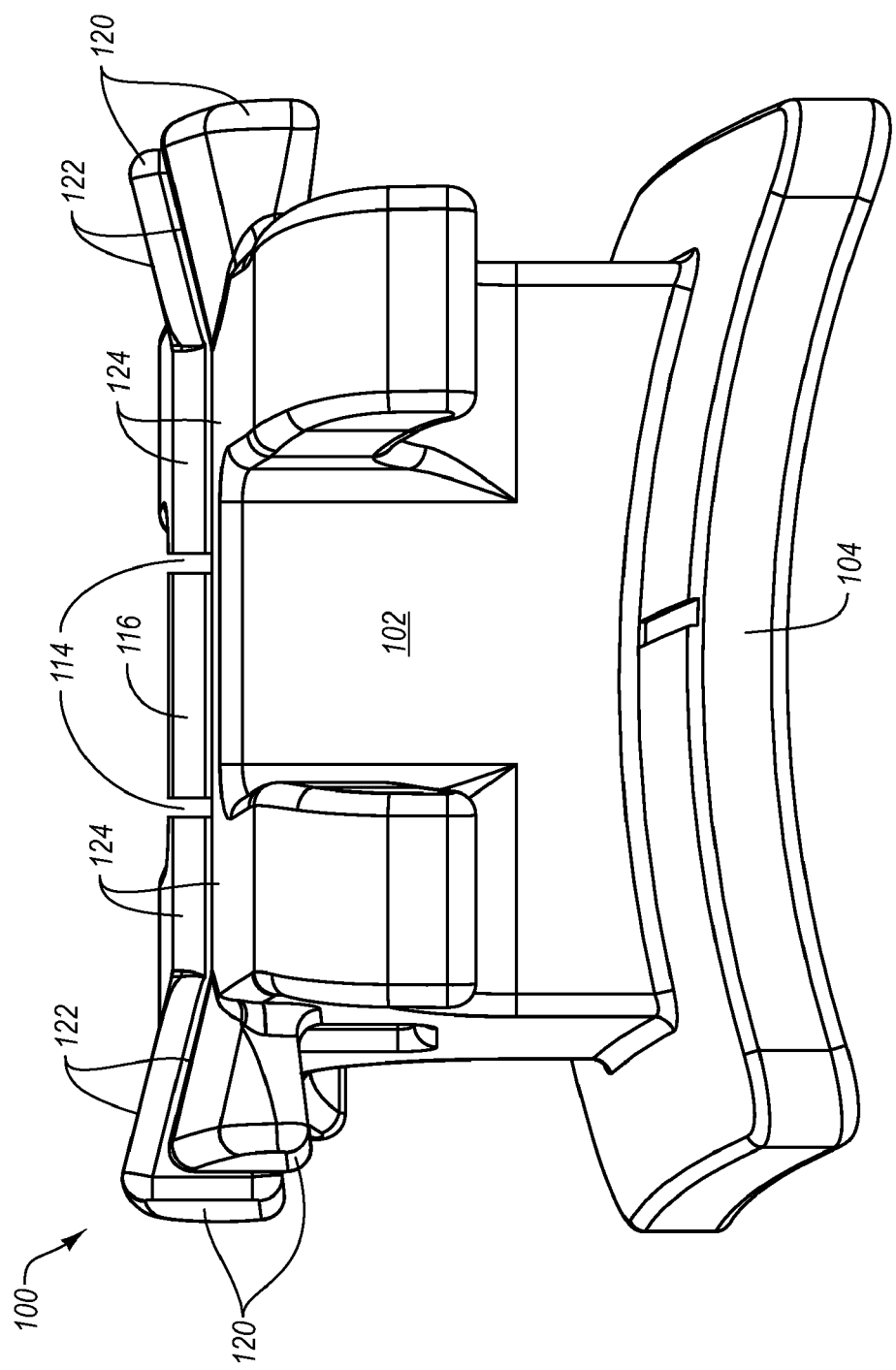
FIG. 2A is a side perspective view of the bracket of FIG. 1.
Figure 2B:
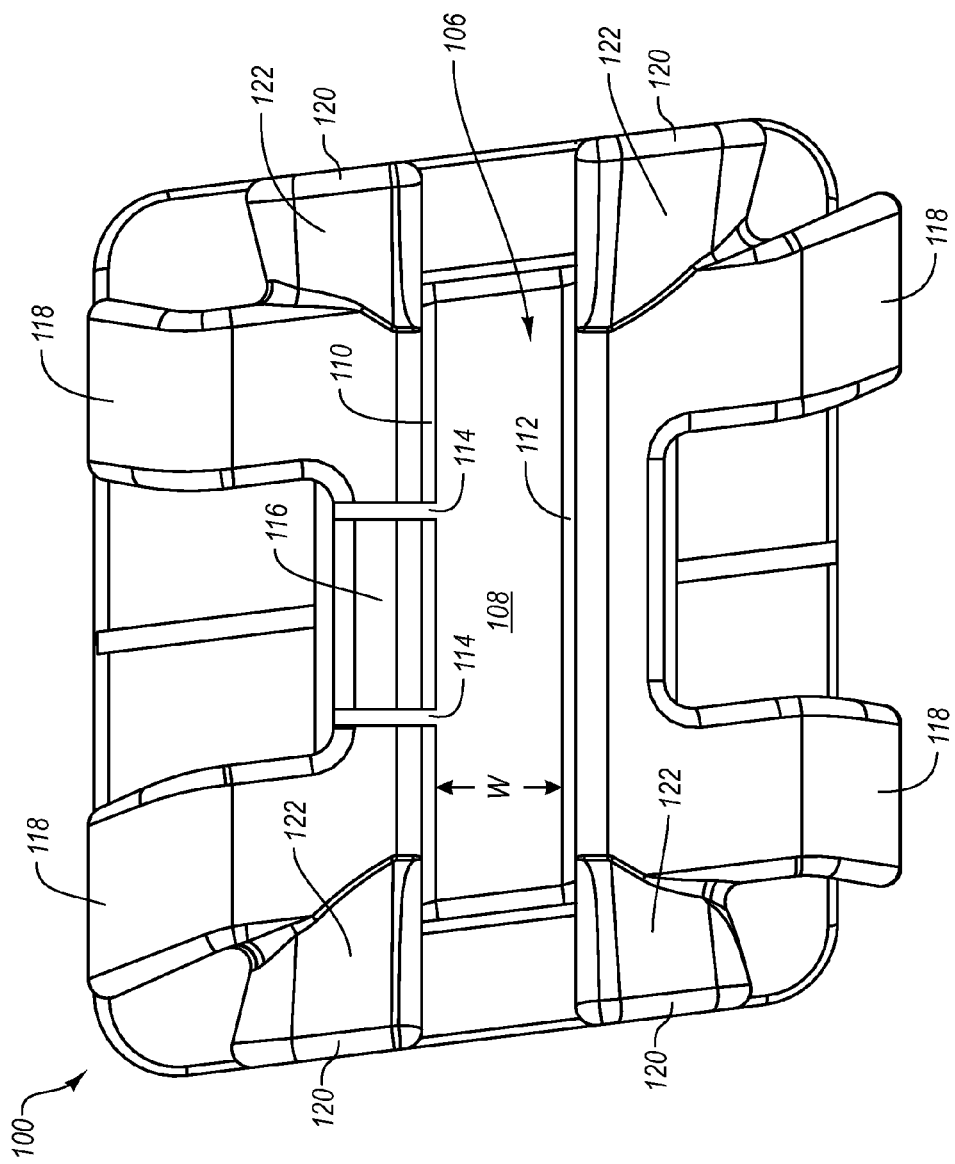
FIG. 2B is a labial top view of the bracket of FIG. 1.

FIGS. 1-2B illustrate an exemplary orthodontic bracket 100 including a bracket base 102. A lingual bonding portion 104 of bracket base 102 is configured for bonding or otherwise being attached to a patient's tooth. Bracket base 102 includes an arch wire slot 106 disposed therein. In the illustrated example, slot 106 is oriented so as to extend mesially-distally within bracket base 102, and is defined by a lingual bottom surface 108, a first side wall 110 and an oppositely disposed second side wall 112. Bracket 100 is illustrated as a non-self-ligating bracket, including four tie wings 118 in which a pair of tie wings 118 extend gingivally from one side of bracket base 102 and side wall 110 and a pair of oppositely disposed tie wings extend occlusally from an opposite side of bracket base 102 and side wall 112.

In the illustrated embodiment, arch wire slot 106 initially has a width W (FIG. 2B) that is substantially constant across the full mesial-distal length of slot 106. First side wall 110 includes two (there could be more) cuts 114 extending from a labial top surface of side wall 110 down to lingual bottom surface 108 so as to define a bendable portion 116 disposed at or near a central portion of wall 110 along slot 106 between cuts 114. In the illustrated embodiment, cuts 114 are illustrated as being substantially parallel to each other and perpendicular to slot 106 (i.e., cuts 114 extend in a lingual-labial direction when bracket 100 is positioned on the tooth). Although illustrated as including cuts 114 within gingival side wall 110, cuts or discontinuities 114 could alternatively be formed within opposite side wall 112.

In order for bendable portion 116 to be bendable, preferably bracket 100 (or at least bendable portion 116) is formed of a metal or other bendable material. Examples of suitable metals include, but are not limited to, stainless steel, stainless steel alloys, titanium, and nickel-titanium alloys. In addition, the metal may contain silver so as to advantageously release silver ions during use, which ions have been shown to have an antimicrobial effect. The metal may be substantially nickel free or alternatively coated, for example with a di-para-xylene coating (e.g. PARYLENE) so as to prevent leaching of nickel (to which some patients are allergic), as well as providing other advantageous properties. For example, such coating may also minimize or prevent galvanic action/corrosion issues that may result because of dissimilar metals within the mouth. A PARYLENE coating exhibits a very low coefficient of friction (e.g. about 0.25), which reduces sliding friction between an arch wire and the bracket slot 106. Such a coating may also minimize or prevent calcification problems, as calcium or other minerals will not as readily adhere and deposit on the coated bracket. PARYLENE also exhibits good optical properties, so that the coated brackets may show less staining compared to non-coated brackets. An alternative configuration that may formed of a polymeric resin, a glass, and/or a ceramic material is shown below in conjunction with FIGS. 7A-7E. Of course, the embodiment of FIGS. 7A-7E may also be formed of metal. Exemplary ceramic materials include, but are not limited to, aluminous oxide, zirconia, and porcelain. Exemplary polymeric resin materials include numerous thermoplastic materials including polyamides (crystalline or amorphous), acetal polymers, polyetherimides, polycarbonates, polyarylether ketones, polysulfones, polyphenylsulfones, and combinations thereof In one embodiment, it may be possible to place a single discontinuity (i.e., cut) within a sidewall so as to define a bendable portion adjacent a mesial or distal edge of the sidewall, although it is preferred to use two or more cuts so as to position the bendable portion symmetrically relative to the length of the arch wire slot (e.g. at or near a center, or two bendable portions positioned at both mesial and distal sides).

In the illustrated embodiment, bendable portion 116 is disposed at or near the center along the length of slot 106 and bendable portion 116 represents only a relatively small fraction of the overall length of arch wire slot 106. For example, bendable portion 116 preferably has a length that is no more than about 75 percent of the overall length of arch wire slot 106, more preferably no more than about 50 percent of the overall length of arch wire slot 106, and most preferably no more than about 30 percent of the overall length of arch wire slot 106. For example, in the illustrated embodiment, the length of bendable portion 116 is about 30% of the length of slot 106. Such a configuration provides a length along which an arch wire within slot 106 is engaged by bendable portion 116, but reduces the length of contact so as to balance the need to provide contact so as to transfer torquing forces sufficient to effect tooth movement, but while minimizing unnecessary contact so as to at the same time reduce sliding friction between the arch wire and the arch wire slot 106 of bracket 100 for increased comfort.

Illustrated bracket 100 further includes a plurality of tie wings (e.g. four), with a pair of tie wings 118 extending gingivally from bracket base 102 and an oppositely disposed pair of tie wings 118 extending occlusally from bracket base 102. In the illustrated embodiment, tie wings 118 each extend from side walls 110 and 112, respectively. In addition to tie wings 118, bracket 100 further includes a plurality (e.g. four) of end wing extensions 120 disposed near the mesial and distal ends of arch wire slot 106. A pair of extensions 120 extend mesially from a mesial side surface and top labial surface of bracket 100, while another pair of extensions are disposed on an opposite side of bracket 100 so as to extend distally from a distal side surface and top labial surface of bracket 100.

As perhaps best seen in FIG. 2A, a top labial surface 122 of each extension 120 preferably extends outwardly from top labial surface 124 of bracket base 102 and sidewalls 110, 112 so as to be labially inclined towards the extreme mesial and distal side surfaces of extensions 120. In one embodiment, the angle of inclination between top labial surface 122 and top labial surface 124 of bracket body 102 is between about 5 degrees and about 30 degrees, more preferably between about 8 degrees and about 25 degrees, and most preferably between about 10 degrees and about 20 degrees. Such an inclination aids in retaining a ligature on top labial surface 122 of extensions 120 so as to prevent a ligature from being inadvertently pushed off surface 122, converting the treatment scheme from passive to active ligation. Additional details of the use of extensions 120 are described in further detail below in conjunction with FIGS. 4A-5B.

Figure 3C:
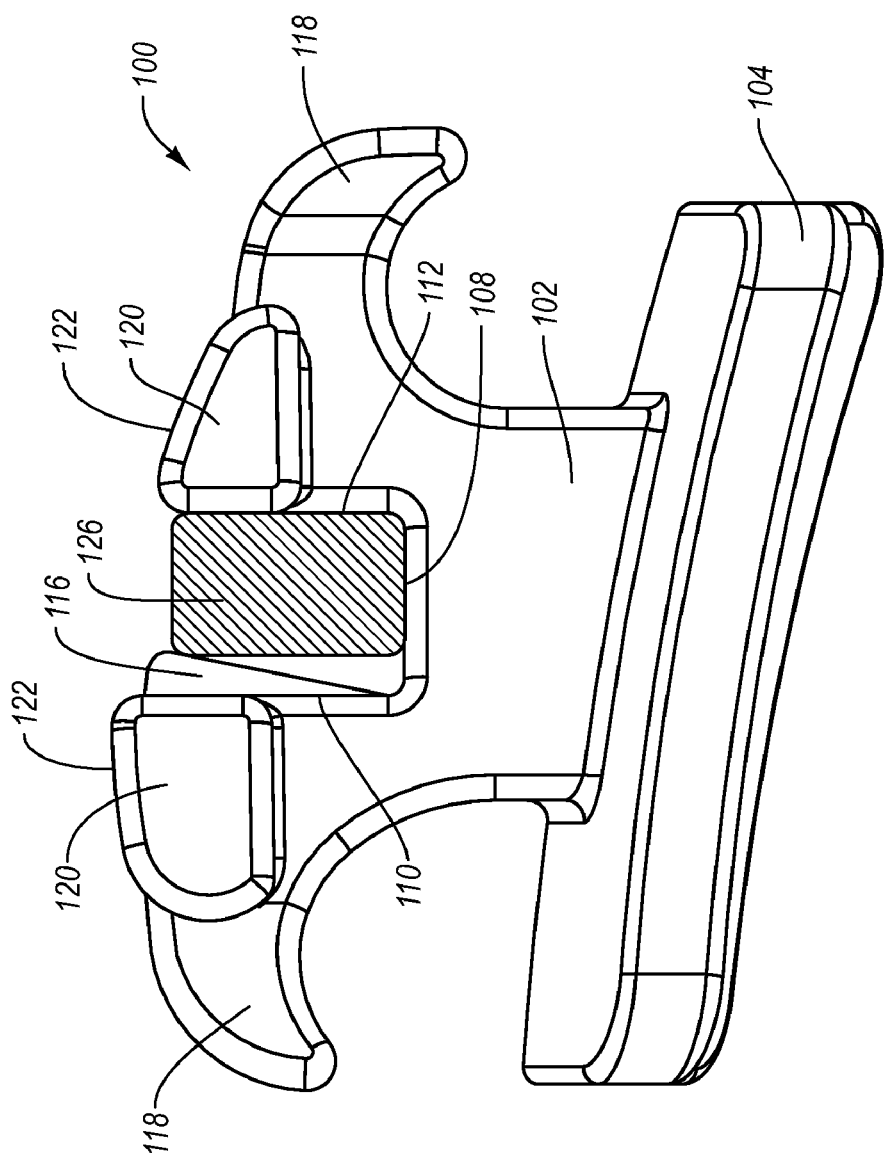
FIG. 3C is a side view of the bracket and arch wire of FIG. 3B.

FIGS. 3A-3C illustrate use of bracket 100 with an under-sized arch wire 126. For example, in a preferred embodiment, the initial width W (FIG. 2B) across the full length of arch wire slot 106 may typically be either 0.018 or 0.022 inch. An arch wire 126 having a width less than W is inserted within slot 106, as shown in FIG. 3A. For example, in one embodiment arch wire 126 may have a width that is between about 3 percent and about 50 percent smaller than the width W of slot 106, more preferably between about 5 percent and about 30 percent smaller than the width W of slot 106, and most preferably between about 10 percent and about 25 percent smaller than the width W of slot 106. For example, if slot 106 has a continuous width that initially measures about 0.018 inch, the inventors have found that employing an arch wire 126 having a width of about 0.016 inch or about 0.014 inch is particularly preferred. Some practitioners may even select an arch wire 126 having a width of about 0.012 inch or smaller. In another example, if slot 106 has a continuous width that initially measures about 0.022 inch, the inventors have found that employing an arch wire 126 having a width of about 0.018 inch or about 0.016 inch is particularly preferred. Some practitioners may even select an arch wire 126 having a width of about 0.014 inch or smaller.

Bendable portion 116 may be selectively bent inwardly as shown in FIGS. 3B-3C so as to reduce the slot width of arch wire slot 106 along the length of bendable portion 116 and engage the arch wire 126 with bendable portion 116. It may be preferred for the practitioner to bend portion 116 inwardly after insertion of arch wire 126, although bending may alternatively be performed prior to insertion, or even during manufacture of the bracket. It is noted that in this configuration, there is little or no engagement between sidewall 110 and arch wire 126 except along bendable portion 116, which in the illustrated embodiment represents only a fraction (e.g. about 30%) of the full length of side wall 110. The bendable portion 116 maintains its bent configuration as a result of the strength of the material (e.g. metal) from which portion 116 is formed, minimizing any tendency for portion 116 to return to its initial unbent configuration as a result of forces applied by an arch wire.

The combination of the smaller arch wire, as well as the limited engagement of arch wire 126 with first side wall 110 (i.e., contact is limited to bendable portion 116) substantially reduces sliding friction as well as the level of force delivered by the arch wire to bracket 100 and the underlying tooth to effect movement. The result is more comfortable treatment accomplished within approximately the same time as compared to if an arch wire having a larger width were employed. Advantageously, the bracket further allows replacement of the arch wire 126 with a standard width arch wire (e.g. an arch wire having a width of 0.018 or 0.022 inch—the same as the width W of slot 106) if a larger force is required either prior to or after use of the undersized arch wire 126. Replacement of the bracket with another bracket is not required, as the width of arch wire slot 106 is adjustable so as to accommodate and engage both undersized wires and conventional sized wires. Such functionality would not be possible with a bracket that simply included an arch wire slot having a reduced but non-adjustable width (e.g. a slot having a width of 0.014 inch), as such a bracket could not accommodate an arch wire of typical width.

Figure 4A:
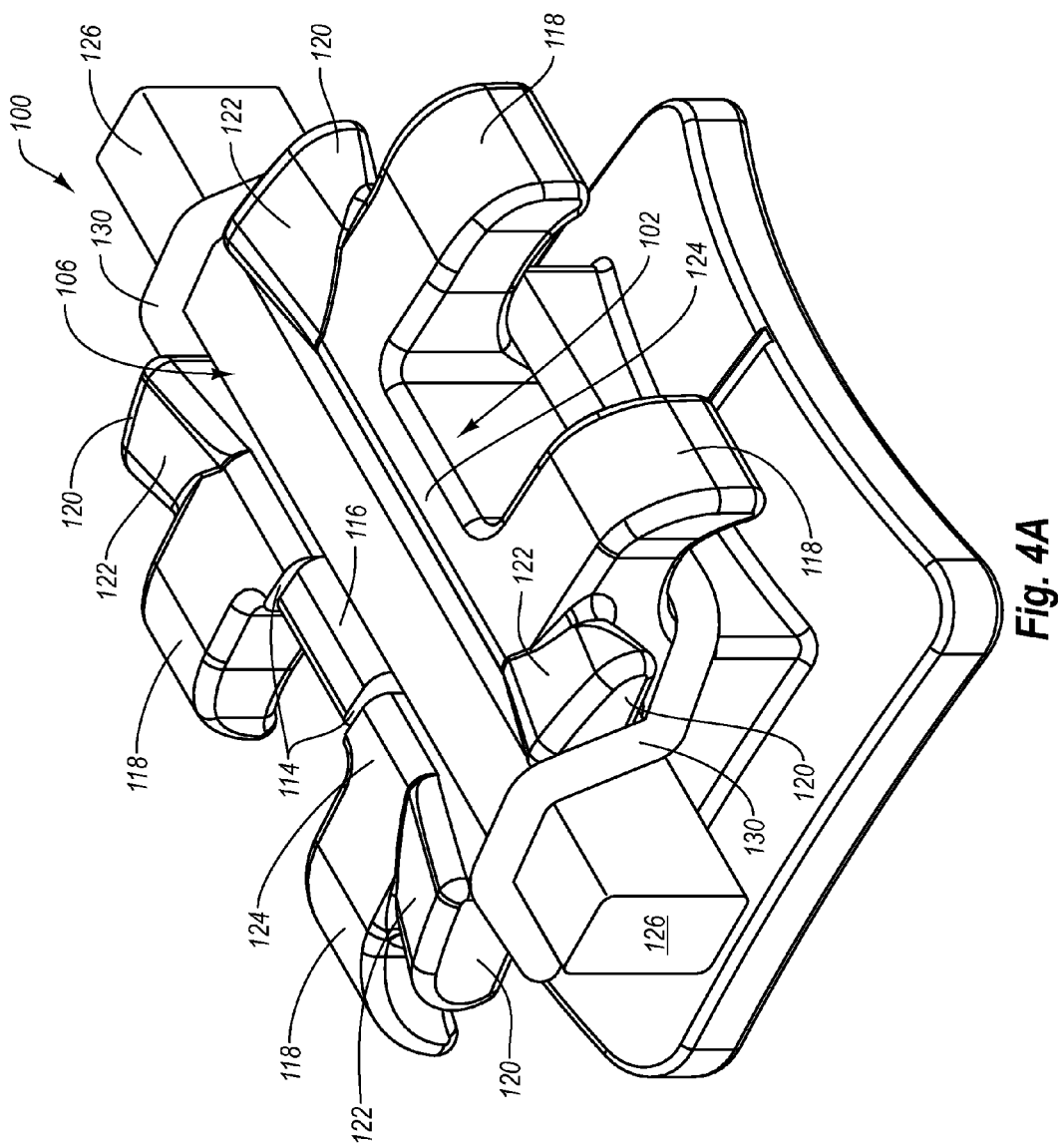
FIG. 4A is an isometric view of the bracket of FIG. 1, in which an arch wire is actively ligated within the arch wire slot of the bracket.

FIGS. 4A-5B illustrate use of the bracket 100 with a ligature 130 positioned to retain arch wire 126 within slot 106. Although illustrated as an elastomeric O-ring ligature 130, other types of ligatures may alternatively be used (e.g. a wire ligature). FIGS. 4A and 4B illustrate an active ligation configuration in which the arch wire 126 is contacted by ligature 130 near the mesial and distal ends of bracket 100 so that arch wire 126 is firmly pressed downward (i.e., lingually) in arch wire slot 106 towards lingual bottom surface 108. Ligature 130 is wrapped under tie wings 118 and over the mesial and distal portions of arch wire 126 so that ligature 130 contacts the top labial surface of arch wire 126, firmly pressing arch wire 126 downward into slot 106, against bottom lingual surface 108 of slot 106. In such a configuration, sliding friction is increased between the surfaces of slot 106 (i.e., surface 108, side wall 112, and bendable portion 116 of side wall 110) and arch wire 126 as a result of contact between ligature 130 and arch wire 126. In addition, there is additional sliding friction as a result of the actual contact between ligature 130 and arch wire 126.

Figure 4B:
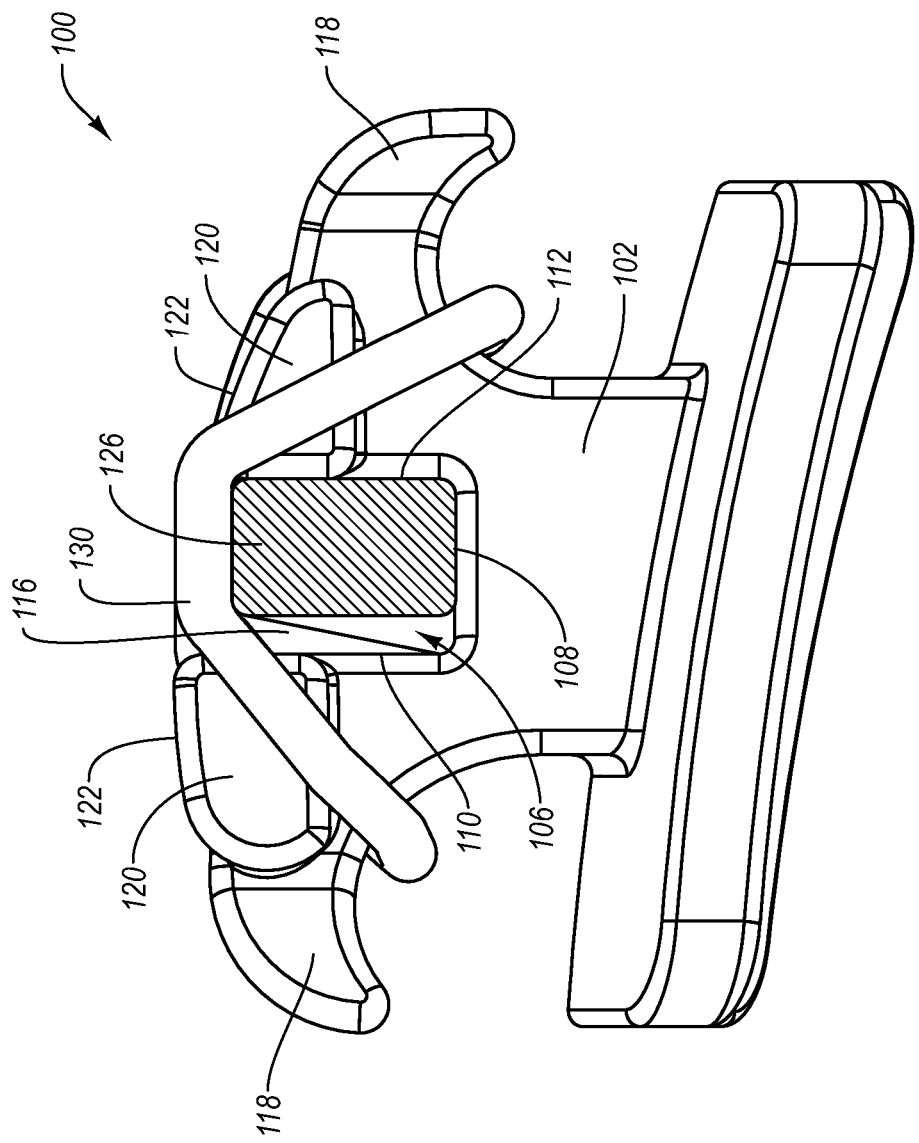
FIG. 4B is a side view of the bracket, arch wire and ligature of FIG. 4A.
Figure 5A:
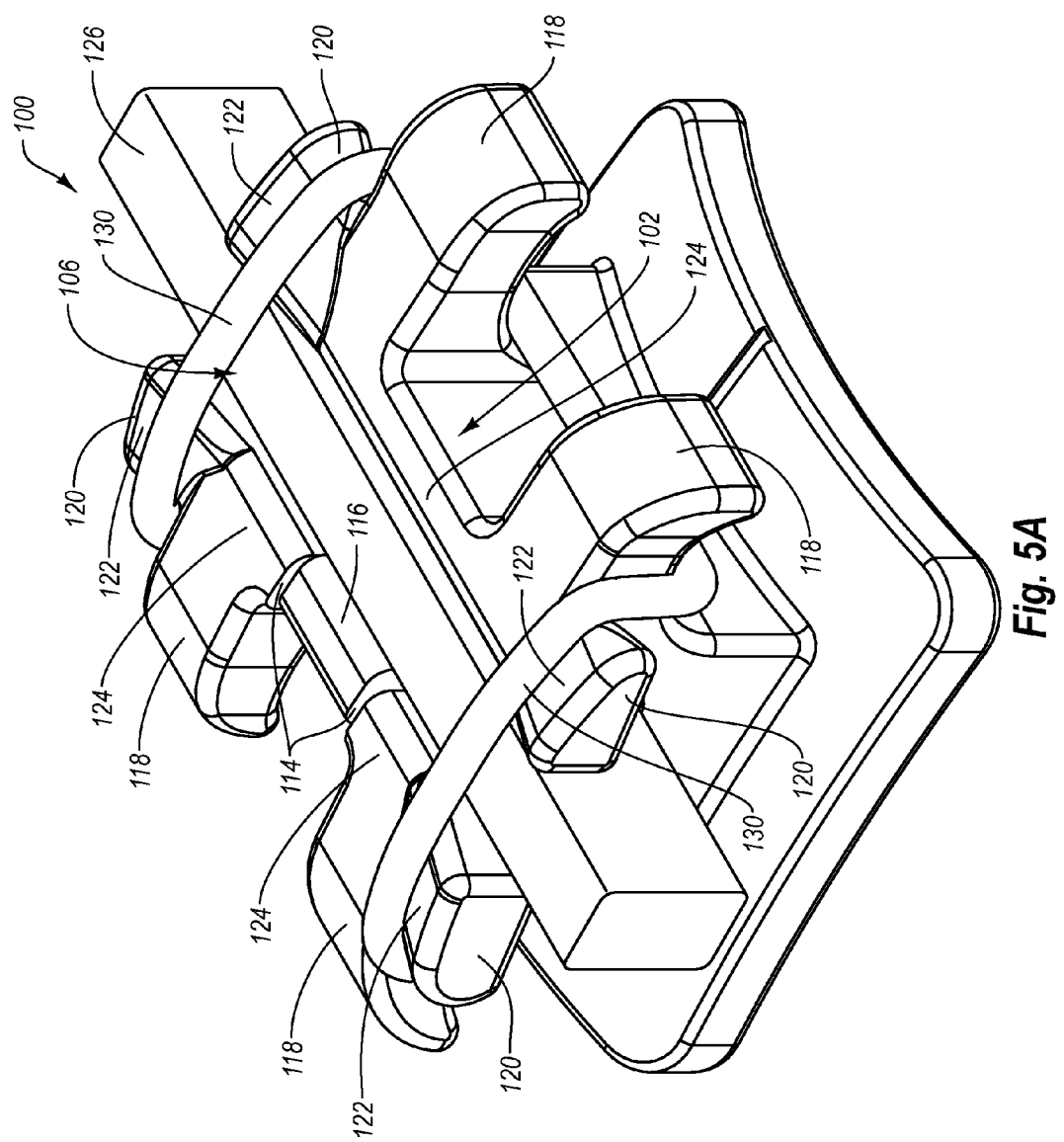
FIG. 5A is an isometric view of the bracket of FIG. 1, in which an arch wire is passively ligated within the arch wire slot of the bracket.
Figure 5B:
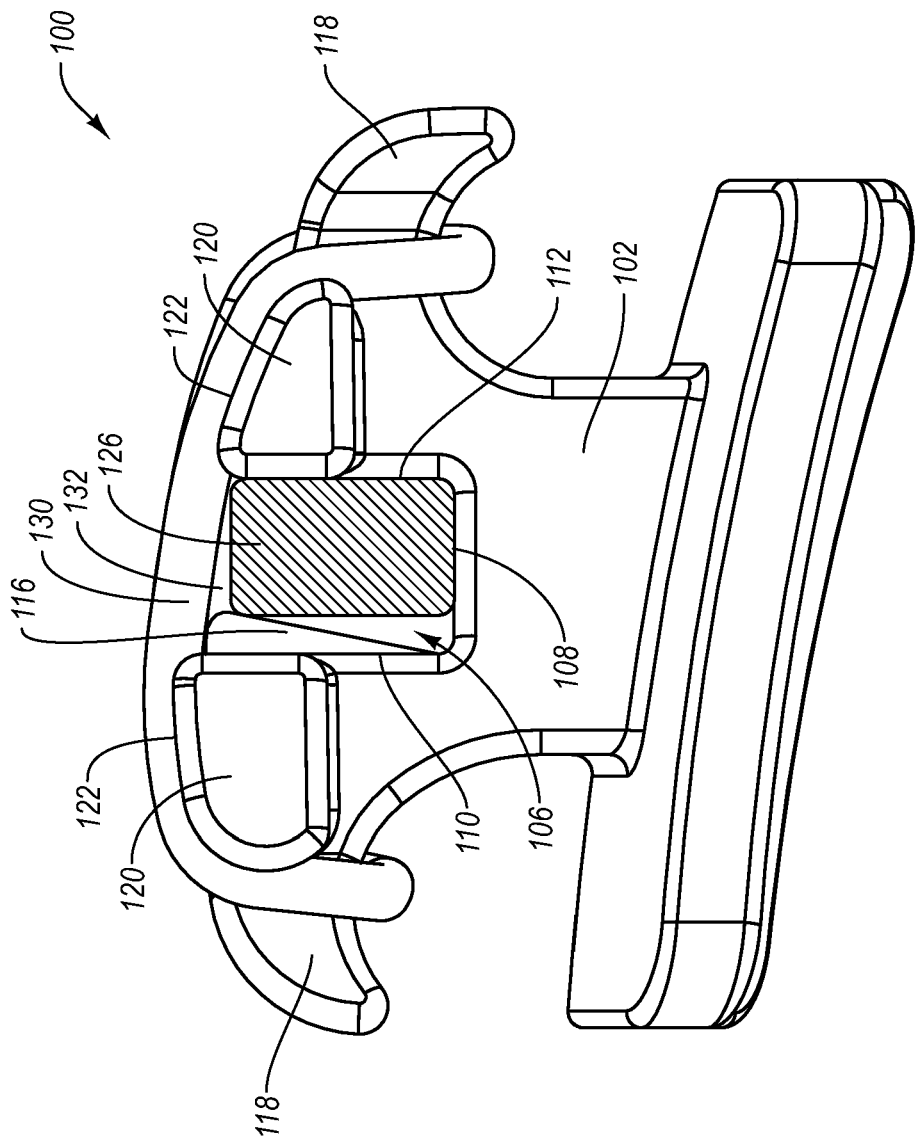
FIG. 5B is a side view of the bracket, arch wire and ligature of FIG. 5A.

FIGS. 5A-5B illustrate an alternative passive ligation configuration that may be accomplished with the same bracket 100 and ligature 130. Relative to the configuration of FIGS. 4A-4B, the portions of ligature 130 that are positioned near the mesial and distal ends of bracket 100 are lifted off arch wire 126 and up onto the top labial surfaces 122 of end wing extensions 120. As perhaps best seen in FIG. 5B, such a configuration creates a space 132 between arch wire 126 and ligature 130. In other words, there is substantially no contact between arch wire 126 and ligature 130, particularly at the mesial and distal ends of bracket 100. The lack of contact between ligature 130 and arch wire 126 provides a configuration in which arch wire 126 is still trapped within slot 106, but friction between slot 106 of bracket 100 (e.g. bendable portion 116 of sidewall 110, sidewall 112, and bottom surface 108) and arch wire 126 is significantly reduced. Such a configuration allows arch wire 126 to slide more freely within slot 106, particularly in a mesial-distal direction defined by the longitudinal axis of the arch wire 126. Necessary corrective forces are still delivered by the arch wire 126 through bracket 100 (e.g. by contact of arch wire 126 with surfaces 108, 112, and bendable portion 116 of sidewall 110). The result of such a passive ligation configuration is increased comfort to the patient. Bracket 100 advantageously allows conversion between active and passive ligation, as desired.

As seen in FIGS. 2A, 4A and 5A, the top labial surface 122 of end wing extensions 120 may advantageously be angled so that the angle of inclination between top labial surface 122 and top labial surface 124 of bracket body 102 is between about 5 degrees and about 30 degrees, more preferably between about 8 degrees and about 25 degrees, and most preferably between about 10 degrees and about 20 degrees. For example, the illustrated bracket includes an inclination angle of about 15 degrees. Such an inclination aids in retaining ligature 130 on top labial surface 122 of extensions 120 so as to prevent ligature 130 from being inadvertently pushed off surface 122, converting the treatment scheme from passive (FIGS. 5A-5B) to active ligation (FIGS. 4A-4B). As such, an active (although simple and fast) step is required by the practitioner in order to convert the ligation scheme from active to passive or vice-versa so as to prevent inadvertent switching from one ligation scheme to another.

Figure 6A:
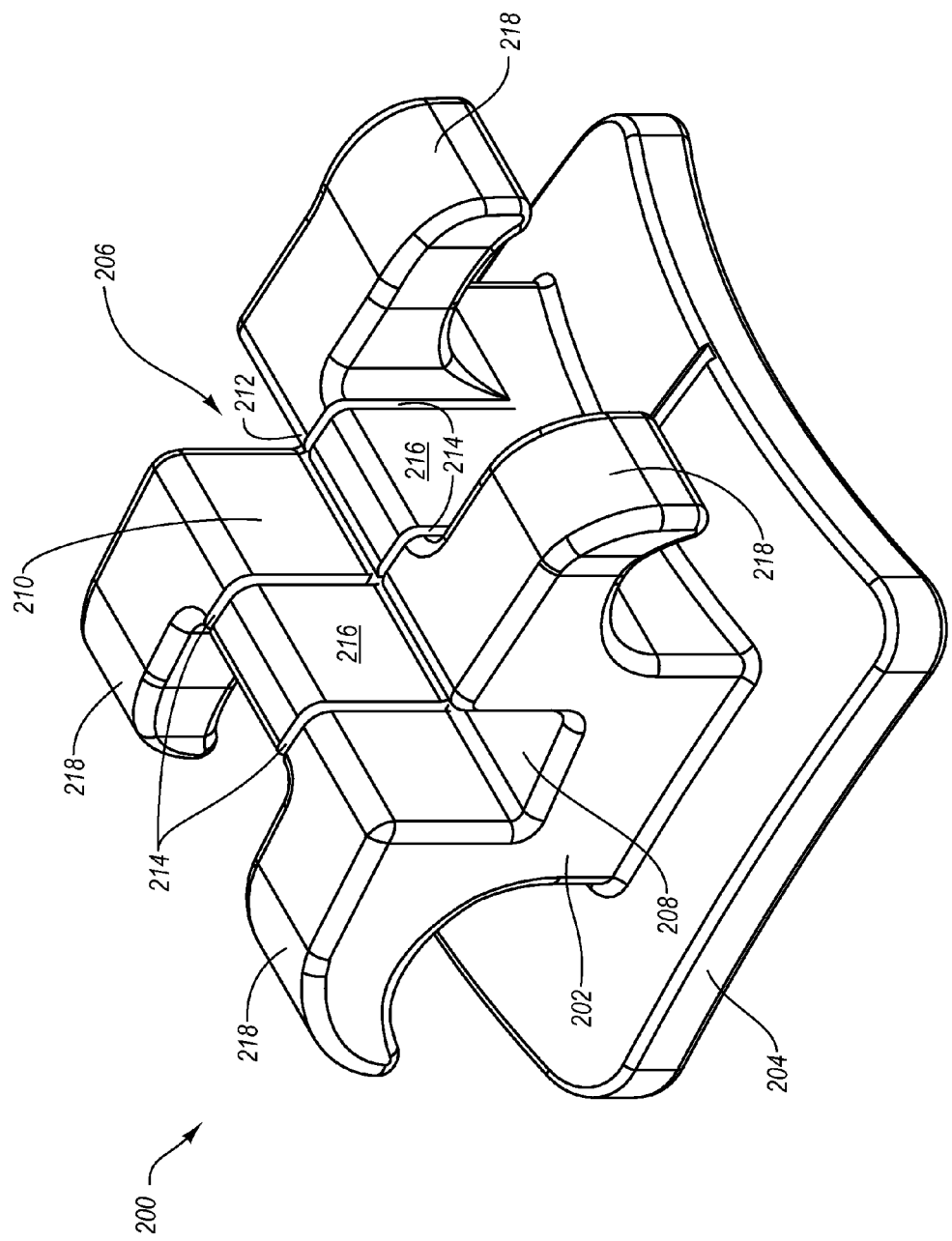
FIG. 6A is an isometric view of an exemplary bracket that includes side cuts on both sidewalls for increased adjustability.
Figure 6B:
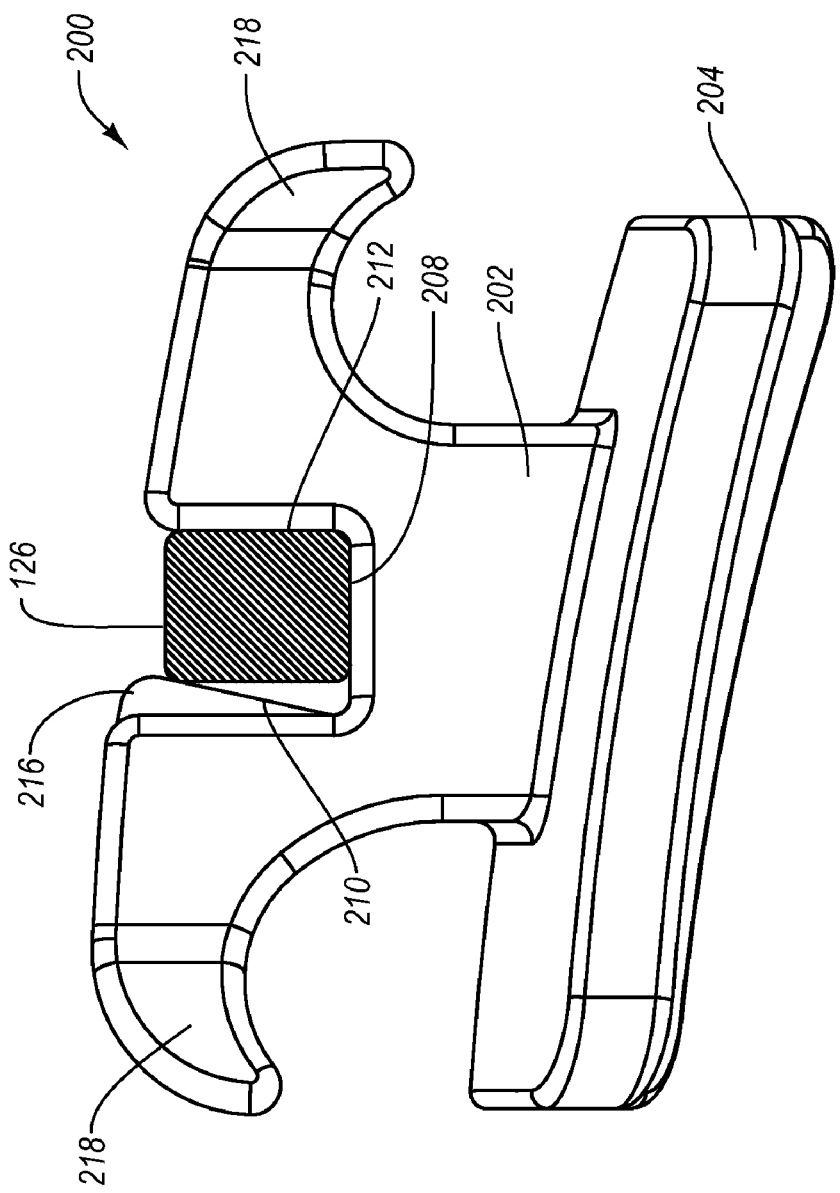
FIG. 6B is a side view of the bracket of FIG. 6A with an arch wire in the slot.
Figure 7A:
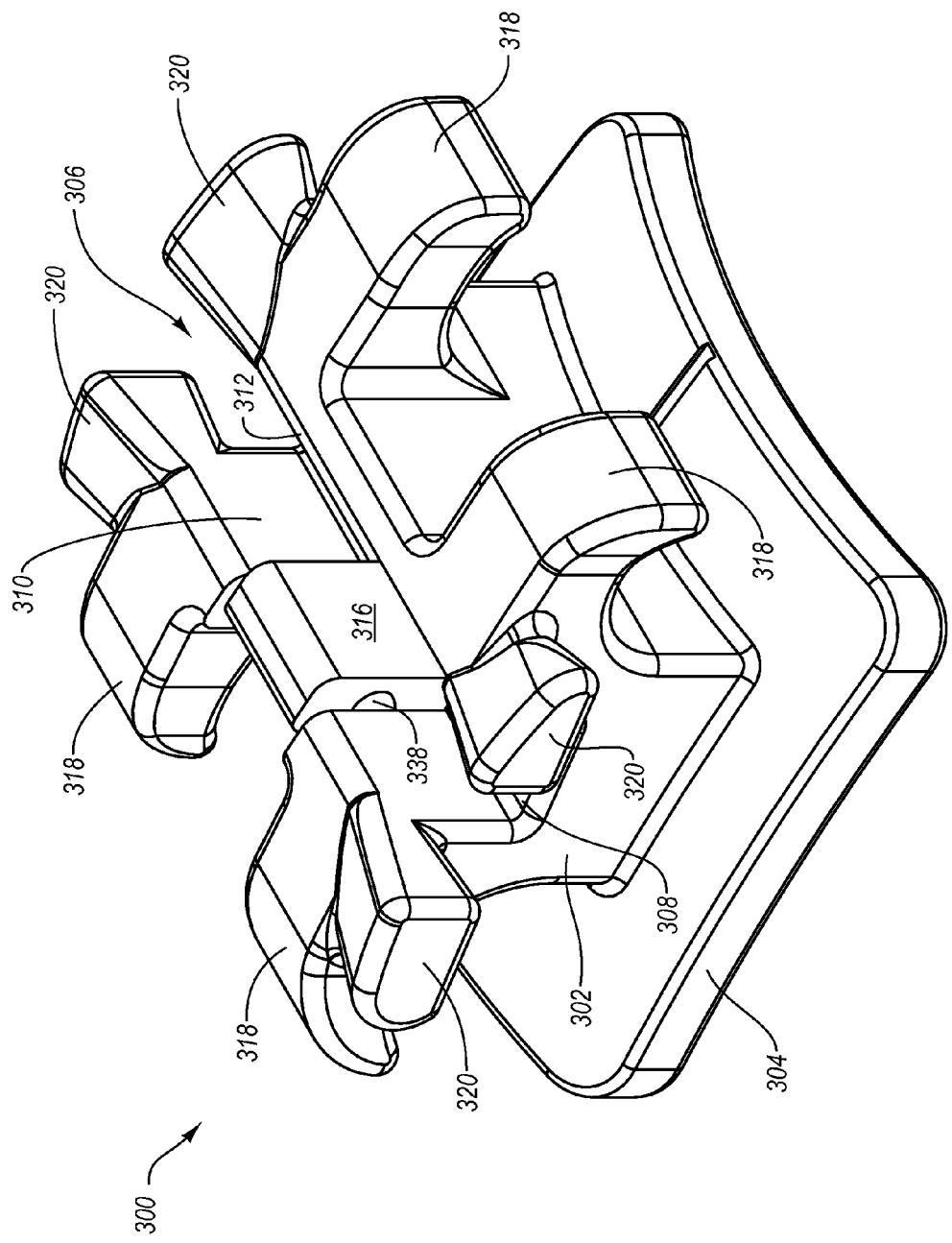
FIG. 7A is an isometric view of another exemplary bracket that includes means for selectively narrowing a width of at least a portion of the arch wire slot.
Figure 7D:
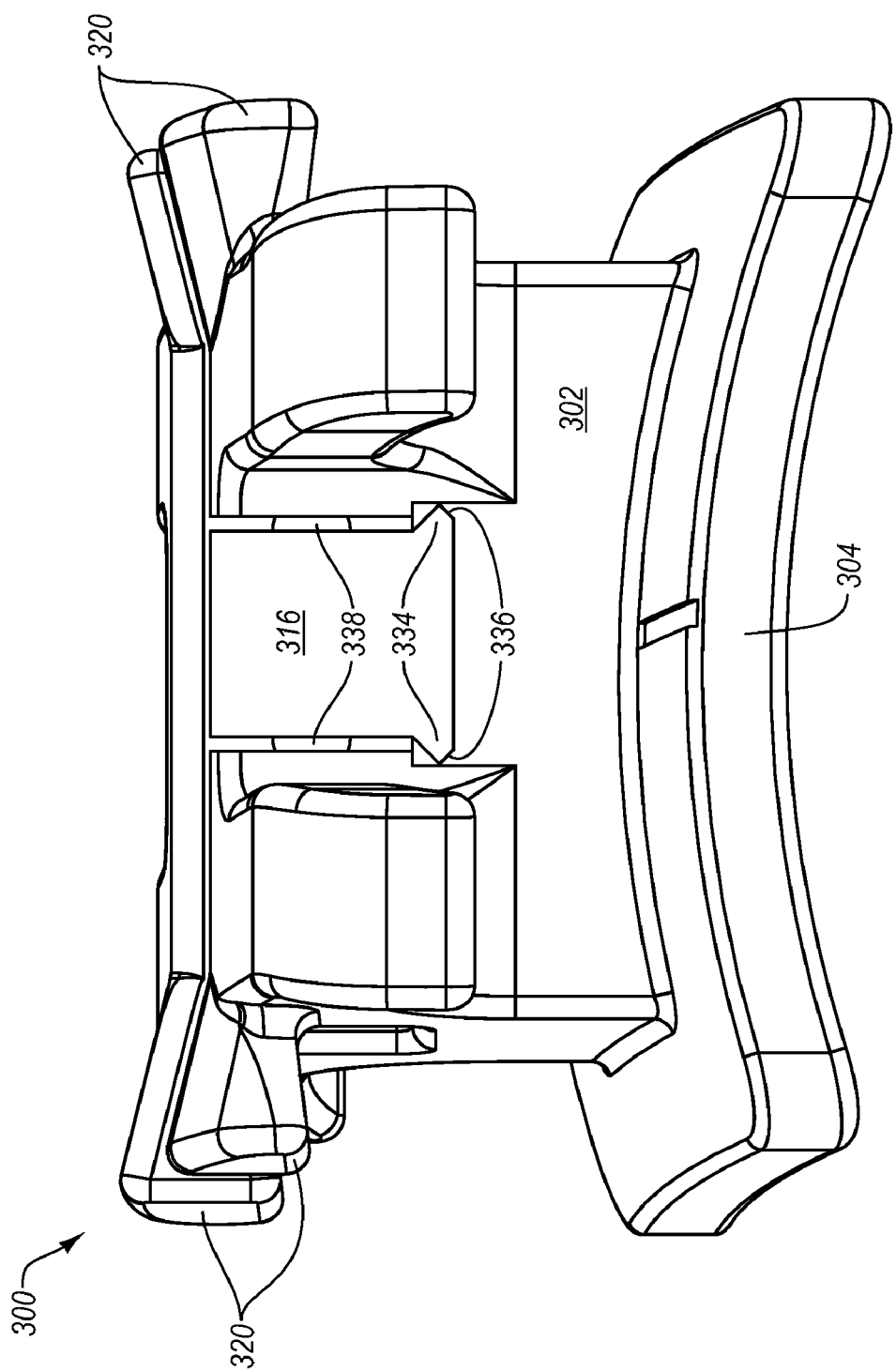
FIG. 7D is a front elevation view of the bracket of FIGS. 7A and 7B illustrating how the movable portion of FIG. 7C may be slidably retained by the bracket.
Figure 7E:
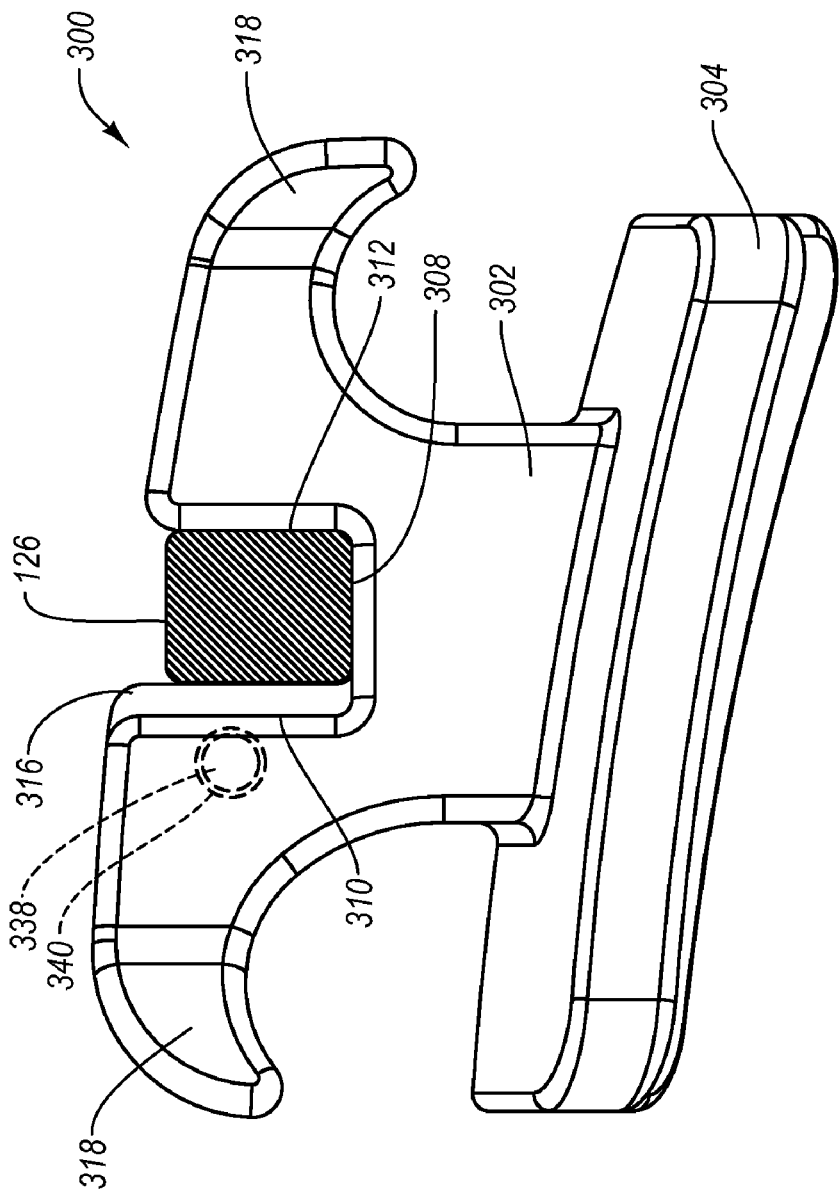
FIG. 7E is a side view of the bracket of FIGS. 7A-7B with an arch wire in the slot.

FIGS. 6A-6B illustrate an alternative embodiment of a bracket 200 according to the present invention, which includes a bracket base 202, a lingual bonding portion 204, an arch wire slot 206 defined by a lingual bottom surface 208, a first side wall 210 and an oppositely disposed second side wall 212. Bracket 200 also includes four tie wings 218 in which a pair of tie wings 218 extend gingivally from one side of bracket base 202 and side wall 210 and a pair of oppositely disposed tie wings extend occlusally from an opposite side of bracket base 202 and side wall 212.

In the illustrated embodiment, arch wire slot 206 initially has a width W (FIG. 6B) that is substantially constant across the full mesial-distal length of slot 206. One principal difference between the embodiment of FIG. 1 and that of FIGS. 6A-6B is that each of side walls 210 and 212 include two cuts 214 extending from a labial top surface of the side wall down to lingual bottom surface 208 so as to define two bendable portions 216. Each of bendable portions 216 in walls 210 and 212 are disposed at or near a central portion of one of respective walls 210 or 212 along slot 206 between cuts 214. In the illustrated embodiment, cuts 214 are illustrated as being substantially parallel to each other and perpendicular to slot 206 (i.e., cuts 214 extend in a lingual-labial direction when bracket 200 is positioned on the tooth), although the cuts or other discontinuities 214 may be configured differently (e.g. angled so as to not be substantially perpendicular) within any of the inventive brackets so long as the cut(s) or discontinuities provide for a bendable portion within at least one sidewall.

In the illustrated embodiment, each bendable portion 216 is disposed at or near the center along the length of slot 206. Positioning bendable portion 216 at or near a center location provides for increased control to arch wire 126 (as compared to if the bendable portion were shifted towards the mesial or distal direction). Of course, it is within the scope of the invention to provide one or more bendable portions anywhere along the length of the arch wire slot. An embodiment as illustrated in FIGS. 6A-6B provides for greater flexibility for the practitioner, as either bendable portion 216 may be bent inwardly, forcing an arch wire 126 against the opposite side wall (in which the opposite bendable portion 216 is preferably not bent inwardly). It is preferred in such an embodiment to only bend one portion 216 inwardly so as to allow arch wire 126 to engage fully with the opposing side wall and bottom surface 208.

Although bracket 200 is illustrated without end wing extensions, such structures may be included in the bracket so as to allow for conversion from active to passive ligation with the same bracket.

FIGS. 1-6B illustrate an embodiment of the bracket in which the means for selectively narrowing a width of at least a portion of the arch wire slot comprises one or more cuts disposed in at least one of the sidewalls defining a bendable portion of the sidewall. FIGS. 7A-7E illustrate an alternative means for selectively narrowing a width of at least a portion of the arch wire slot. Bracket 300 includes a bracket base 302, a lingual bonding portion 304, an arch wire slot 306 defined by a lingual bottom surface 308, a first side wall 310 and an oppositely disposed second side wall 312. Bracket 300 also includes four tie wings 318 in which a pair of tie wings 318 extend gingivally from one side of bracket base 302 and side wall 310 and a pair of oppositely disposed tie wings extend occlusally from an opposite side of bracket base 302 and side wall 312. Bracket 300 is also illustrated as including end wing extensions 320.

As illustrated, arch wire slot 306 initially has a width W (FIG. 7B) that is substantially constant across the full mesial-distal length of slot 306, and may be narrowed by laterally movable portion 316. In the illustrated embodiment, movable portion 316 is disposed at or near the center of sidewall 310 along the length of slot 306. Positioning movable portion 316 at or near a center location provides for increased control to the arch wire 126 (as compared to if the movable portion were shifted towards the mesial or distal direction). Of course, it is within the scope of the invention to provide one or more movable portions anywhere along the length of the arch wire slot.

In the illustrated embodiment, movable portion 316 is slidably coupled with bracket base 302. For example, the illustrated embodiment includes a sliding engagement mechanism which allows movable portion 316 to slide inwardly relative to the remainder of sidewall 310, narrowing the width of slot 306 adjacent to movable portion 316. Illustrated movable portion 316 includes a pair of laterally extending slide rails 334. Rails 334 are oriented and aligned parallel to one another and are configured to slidingly engage with corresponding structure (e.g. grooves 336) formed in base 302. Movable portion 316 further includes a pair of détentes 338 or other protrusions formed on mesial and distal sides of portion 316 configured to lockingly engage with wells 340 or other recesses formed in side wall 310. Of course the configuration could be reversed (détentes formed in side wall 310, recesses 340 formed on movable portion 316).

Recesses 340 are formed at locations corresponding to the desired location of protrusions 338 when movable portion 316 is at an initial position in which slot 306 is not narrowed, and a secondary position in which slot 306 is narrowed because portion 316 has been slid inwardly. Recesses 340 and protrusions 338 are one example of a locking mechanism for maintaining movable portion 316 in a desired configuration (i.e., preventing unwanted sliding of portion 316 during treatment). Slidable portion 316, in addition to the bendable portions described above, are examples of means for selectively narrowing the arch wire slot. Other locking mechanisms alternative to recesses 340 and protrusions 338, as well as alternative means for selectively narrowing the width of the arch wire slot will be apparent to one skilled in the art.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An orthodontic bracket comprising:
   a bracket base;
   at least one arch wire slot formed in the bracket base adapted to receive an arch wire therein, the arch wire slot having a labial opening and being defined by a pair of sidewalls, each sidewall having a mesial first end and a distal second end and wherein the slot has a main slot width defined by a distance between the sidewalls along a length between the mesial first end and the distal second end; and
   one or more cuts formed through an entire thickness of at least one of the sidewalls between the mesial first end and the distal second end thereof so as to define a bendable portion of the sidewall, the bendable portion providing a variable slot width portion,
   the bendable portion being selectively inwardly bendable by a bendable force such that the bendable portion remains inwardly bent toward an opposing sidewall upon release of the bending force so as to selectively narrow the variable slot width portion relative to the main slot width and bear against an arch wire that is positionable in the arch wire slot and which has a width that is less than the main slot width.

2. An orthodontic bracket as recited in claim 1, wherein the bendable portion has a length that is no more than about 75 percent of the overall length of the arch wire slot.

3. An orthodontic bracket as recited in claim 1, wherein the bendable portion has a length that is no more than about 50 percent of the overall length of the arch wire slot.

4. An orthodontic bracket as recited in claim 1, wherein the bendable portion has a length that is no more than about 30 percent of the overall length of the arch wire slot.

5. An orthodontic bracket as recited in claim 1, wherein the bracket base further comprises a plurality of tie wings extending outwardly therefrom.

6. An orthodontic bracket as recited in claim 5, wherein the bracket is a twin bracket including two pairs of tie wings.

7. An orthodontic bracket as recited in claim 5, further comprising a plurality of end wing extensions disposed on the bracket base and extending outwardly in a direction parallel to a longitudinal axis of the arch wire slot, the end wing extensions being configured to selectively allow placement of a ligature so as to selectively provide active ligation or passive ligation of the arch wire within the arch wire slot.

8. An orthodontic bracket as recited in claim 7, wherein a top labial surface of each end wing extension is upwardly inclined towards the mesial and distal ends of the end wing extensions so that during passive ligation use, a ligature contacts the top labial surface of each end wing extension and is guided towards a center of the bracket so as to minimize inadvertent sliding of a ligature off the inclined mesial and distal ends of the extensions.

9. An orthodontic bracket as recited in claim 8, wherein an angle of inclination between the top labial surface of each end wing extension and a top labial surface of the bracket body is between about 5 degrees and about 30 degrees.

10. An orthodontic bracket as recited in claim 8, wherein an angle of inclination between the top labial surface of each end wing extension and a top labial surface of the bracket body is between about 8 degrees and about 25 degrees.

11. An orthodontic bracket as recited in claim 8, wherein an angle of inclination between the top labial surface of each end wing extension and a top labial surface of the bracket body is between about 10 degrees and about 20 degrees.

12. An orthodontic bracket comprising:
a bracket base;
at least one arch wire slot formed in the bracket base adapted to receive an arch wire through a labial opening of the slot, the arch wire slot being defined by a pair of sidewalls; and
one or more cuts formed through an entire thickness of only one of the sidewalls so as to define a bendable sidewall portion and a stationary sidewall portion adjacent to the bendable sidewall portion, the stationary sidewall portion together with an opposite sidewall defining a fixed slot width portion, the bendable portion being selectively inwardly bendable by a bending force such that the bendable portion remains inwardly bent upon release of the bending force so as to define a variable slot width portion that can be selectively narrowed relative to the fixed slot width portion, the bendable portion having an inner surface facing the arch wire slot that is substantially planar prior to being inwardly bent.

13. An orthodontic bracket as recited in claim 12, wherein the bracket base further comprises a plurality of tie wings extending outwardly therefrom.

14. An orthodontic bracket as recited in claim 13, wherein the bracket is a twin bracket including two pairs of tie wings.

15. An orthodontic bracket as recited in claim 13, further comprising a plurality of end wing extensions disposed on the bracket base and extending outwardly in a direction parallel to a longitudinal axis of the arch wire slot, the end wing extensions being configured to selectively allow placement of a ligature so as to selectively provide active ligation or passive ligation of the arch wire within the arch wire slot.

16. An orthodontic bracket as recited in claim 15, wherein a top labial surface of each end wing extension is upwardly inclined towards the mesial and distal ends of the end wing extensions so that during passive ligation use, a ligature contacts the top labial surface of each end wing extension and is guided towards a center of the bracket so as to minimize inadvertent sliding of a ligature off the inclined mesial and distal ends of the extensions.

17. An orthodontic bracket as recited in claim 16, wherein an angle of inclination between the top labial surface of each end wing extension and a top labial surface of the bracket body is between about 5 degrees and about 30 degrees.

18. An orthodontic bracket as recited in claim 16, wherein an angle of inclination between the top labial surface of each end wing extension and a top labial surface of the bracket body is between about 8 degrees and about 25 degrees.

19. An orthodontic bracket as recited in claim 16, wherein an angle of inclination between the top labial surface of each end wing extension and a top labial surface of the bracket body is between about 10 degrees and about 20 degrees.

20. An orthodontic bracket comprising:
a bracket base;
at least one arch wire slot formed in the bracket base adapted to receive an arch wire through a labial opening, the arch wire slot having a fixed slot width portion defined by a sidewall disposed on one side of the slot and a stationary sidewall portion disposed on an opposite side of the slot; and
a moveable sidewall portion adjacent to the stationary sidewall portion that is attached to the bracket base and not the stationary sidewall portion so as to be moveable independently of the stationary sidewall portion in order to provide a variable slot width portion for selectively narrowing a width of a portion of the arch wire slot relative to the fixed slot width portion,
wherein the moveable sidewall portion is substantially smooth without any significant protuberance along an entire length and depth of the moveable sidewall portion prior to narrowing the width of the arch wire slot wherein the orthodontic bracket comprises one or more cuts formed through an entire thickness of at least one of the sidewalls between the mesial and distal end and the distal second end thereof so as to define a bendable portion in at least one of the sidewalls, the bendable portion in one sidewall being the movable sidewall portion, the bendable portion being selectively inwardly bendable by a bending force such that the bendable portion remains inwardly bent upon release of the bending force so as to, effectively narrow at least a portion of the slot width.

* * * * *

UNITED STATES PATENT AND TRADEMARK OFFICE
CERTIFICATE OF CORRECTION

PATENT NO. : 7,857,618 B2  
APPLICATION NO. : 11/945801  
DATED : December 28, 2010  
INVENTOR(S) : Abels et al.

Page 1 of 1

It is certified that error appears in the above-identified patent and that said Letters Patent is hereby corrected as shown below:

Title Page, Right Hand Column Item (74)
Change the Primary Examiner from "Chris L Rodriguez" to --Cris L Rodriguez--

Drawings
Sheet 13, replace Figure 7C with the figure depicted below, wherein the reference numeral "316'" has been changed to --316--

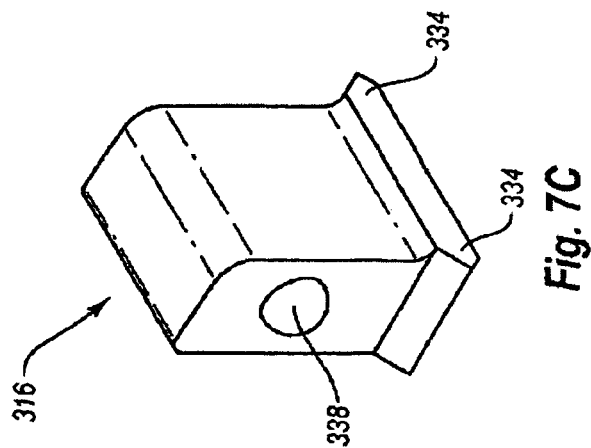

Column 4
Line 47, change "of an the" to --of the--
Line 62, change "receive and arch wire" to --receive an arch wire--

Column 5
Line 53, change "that may formed" to --that may be formed--

Signed and Sealed this
Seventh Day of June, 2011

David J. Kappos
*Director of the United States Patent and Trademark Office*